United States Patent [19]

Briggs et al.

[11] Patent Number: 5,030,766
[45] Date of Patent: Jul. 9, 1991

[54] CATALYSTS FOR PRODUCING 1,3-DIOLS AND/OR 3-HYDROXYALDEHYDES, AND PROCESSES FOR MAKING AND USING SAME

[75] Inventors: John R. Briggs; John M. Maher, both of Charleston; Arnold M. Harrison, So. Charleston, all of W. Va.

[73] Assignee: Technology Corporation, Danbury, Conn.

[21] Appl. No.: 519,446

[22] Filed: May 4, 1990

[51] Int. Cl.$^5$ .................. C07C 27/22; C07C 45/58; C07C 47/263
[52] U.S. Cl. .................. 568/496; 568/449; 568/488; 568/852; 568/867
[58] Field of Search .............. 568/867, 454, 458, 488, 568/449, 852, 496; 502/162

[56] References Cited

U.S. PATENT DOCUMENTS

| | | | |
|---|---|---|---|
| 3,456,017 | 7/1969 | Smith et al. | 568/867 |
| 3,463,819 | 8/1969 | Smith et al. | 568/867 |
| 3,687,981 | 8/1972 | Lawrence et al. | 568/867 |
| 4,322,355 | 3/1982 | Horvitz et al. | 568/867 |
| 4,873,378 | 9/1989 | Murphy et al. | 568/867 |
| 4,873,379 | 9/1989 | Murphy et al. | 568/867 |
| 4,935,554 | 6/1990 | Murphy et al. | 568/867 |

FOREIGN PATENT DOCUMENTS

| | | | |
|---|---|---|---|
| 0257967 | 3/1988 | European Pat. Off. | 568/867 |
| 0306094 | 3/1989 | European Pat. Off. | |

*Primary Examiner*—Werren B. Lone
*Attorney, Agent, or Firm*—Morris N. Reinisch

[57] ABSTRACT

A process for producing a 1,3-diol, e.g., 1,3-propanediol, or a 3-hydroxyaldehyde is disclosed which comprises contacting a combination of an epoxide, carbon monoxide and hydrogen in the present of a rhodium-containing catalyst effective to promote the hydroformylation of the epoxide at conditions effective to form at least one of a 1,3-diol and a 3-hydroxyaldehyde, the contacting occurring in the substantial absence of a promoting amount of alkali metal ions, and at least a portion of the rhodium-containing catalyst being formed substantially without incorporation of the epoxide. A process for producing such rhodium-containing compositions is also disclosed.

31 Claims, No Drawings

CATALYSTS FOR PRODUCING 1,3-DIOLS AND/OR 3-HYDROXYALDEHYDES, AND PROCESSES FOR MAKING AND USING SAME

BACKGROUND OF THE INVENTION

The present invention relates to the production of 1,3-diols and/or 3-hydroxyaldehydes thereof from epoxides. More particularly, the invention relates to hydroformylation catalysts, processes for making hydroformylation catalysts and processes using hydroformylation catalysts for producing such 1-3 diols and/or 3 -hydroxyaldehydes from epoxides.

Glycols in general are valuable chemical compounds which find a wide variety of utilities. Such compounds are used, for example, as chemical intermediates in the manufacture of esters, as well as in the synthesis of polyesters. 1,3-Propanediol, in particular, had been found to be especially useful in a number of applications. 1,3-Propanediol has been prepared by acid-catalyzed hydration of acrolein to form 3-hydroxypropanal which is subsequently hydrogenated to the corresponding glycol. Because of the relatively low reaction rates and low product yields obtained, this approach has not led to a viable process for making 1,3-propanediol in large commercial quantities.

The preparation of 1,3-diols, i.e., 1,3-glycols, by the hydroformylation of epoxides, utilizing phosphine-modified cobalt carbonyl complexes as the catalyst, is disclosed in Smith et al U.S. Pat. No. 3,463,819. In particular, this patent shows the production of 1,3-propanediol by hydroformylation of ethylene oxide, using a tertiary phosphine-modified cobalt carbonyl catalyst. Very high cobalt-containing catalyst concentrations are needed to provide good yields of 1,3-propanediol.

Lawrence et al U.S. Pat. No. 3,687,981 discloses a process for manufacturing 1,3-propanediol which employs two separate stages. In the first stage, ethylene oxide undergoes a hydroformylation reaction in the presence of a hydroformylation catalyst containing a transition metal, particularly metals of Group VIII of the periodic chart, e.g., cobalt carbonyl tertiary phosphine and rhodium carbonyl, to produce 2-(2 hydroxyethyl)-4-hydroxy-1,3-dioxane. The dioxane compound, together with a small amount of 3-hydroxypropionaldehyde, is catalytically hydrogenated to form 1,3- propanediol.

Smith et al U.S. Pat. No. 3,456,017 discloses production of 1,3-propanediol by hydroformylation of ethylene oxide using, as catalyst, dicobalt hexacarbonyl complexes wherein the remaining two coordination sites of the cobalt moieties are complexed with one or more tertiary phosphine ligands.

Horvitz et al U.S. Pat. No. 4,322,355 discloses the reaction of olefin with aldehyde in the presence of a strong acid catalyst and a co-catalyst selected from antimony and bismuth oxides and salts to provide one, or a mixture of, 1,3-difunctional compounds.

European Patent Publication No. 0257967 discloses a process for producing 1,3-glycols by reacting an epoxide with synthesis gas in an acidic medium in the presence of rhodium and a phosphine. This publication discloses a reaction mixture containing (1) the epoxide: (2) rhodium; (3) a phosphine; (4) water; (5) carbon monoxide; (6) hydrogen; and (7) an acid. Although a wide range of acid to rhodium molar ratios is disclosed, e.g., from 10/1 to 1/10, this publication discloses a preference for a molar ratio of acid to rhodium of approximately 1. This publication discloses that an induction period, of about 0.5 to 1 hour or more in duration, occurs after the reaction mixture is formed before gas uptake begins. This "induction period", which itself is wasteful because a larger reactor and/or longer time is required to produce a given amount of 1,3-diol, is in part a result of combining some of the epoxide with the rhodium and phosphine, and possibly other components, to produce the true hydroformylation catalyst. Thus, some of the epoxide is incorporated into the hydroformylation catalyst. Using the epoxide to produce the catalyst reduces the ultimate yield, of desired products, e.g., 1,3-diol. A rhodium-containing catalyst which does not require an induction period and/or which is made without incorporation of epoxide would clearly be advantageous.

Murphy et al U.S. Pat. No. 4,873,378 discloses substantially the same process as that disclosed in the above-noted European Patent Publication. In addition, this patent discloses that a salt having an alkali metal cation and a solubilizing anion is also present in the reaction mixture. This patent discloses that the "induction period" is eliminated in certain examples containing relatively large amounts of alkali metal salts. No salts other than alkali metal salts are suggested.

Murphy et al U.S. Pat. No. 4,873,379 discloses a process for producing 1,3-diols. This patent discloses a reaction mixture containing (1) an epoxide; (2) rhodium; (3) an alkali metal salt promotor; (4) water; (5) carbon monoxide; and (6) hydrogen. No promotors other than alkali metal salts are suggested.

European Patent Publication No. 0306094 discloses a process for the hydroformylation of certain acrylic acid derivatives in the presence of a homogeneous catalyst system comprising a rhodium compound and one or more triphenylphosphites. No epoxide hydroformylation is suggested.

There continues to be a need for a new epoxide hydroformylation catalyst, and for processes for making and using the same, particularly to produce 1,3-diols and/or 3-hydroxyaldehydes.

SUMMARY OF THE INVENTION

A new epoxide hydroformylation process, catalyst for use in such process, and process for producing such catalyst have been discovered. The present epoxide hydroformylation process provides high ultimate yields of desired products, such as 1,3-diols and/or 3-hydroxyaldehydes, which are precursors of such 1,3-diols. Importantly, the present process does not require that the epoxide be incorporated in the catalytic species. Thus, no epoxide need be used in, or even be present during, the making of the catalyst. Further, the catalyst can be produced separate and apart from the hydroformylation reaction mixture. This allows the hydroformylation reactor, which is operated at relatively severe conditions and, therefore, is capital intensive and expensive to operate, to function as a hydroformylation reactor rather than also as a catalyst production facility. In short, the present hydroformylation catalyst compositions and processes provide for substantial benefits, e.g., processing economies and efficiencies, in producing 1,3-diols and/or 3-hydroxyaldehydes.

In one broad aspect, the present invention is directed to a process for producing a 1,3-diol or a 3-hydroxyaldehyde. This process comprises contacting a combination of an epoxide, carbon monoxide and hydrogen in the presence of a rhodium-containing catalyst composition effective to promote the hydroformylation of the epoxide at conditions effective to form at least one of a 1,3-diol and a 3-hydroxyaldehyde. In one embodiment, this contacting occurs in the substantial absence of a promoting amount of alkali metal cations and at least a portion, e.g., at least about 10%, and preferably at least a major portion, i.e., at least about 50%, and more preferably substantially all, of the catalyst composition is formed substantially without the incorporation or inclusion of an epoxide, in particular, the epoxide to be hydroformylated. Thus, as least a portion, preferably a major portion and more preferably substantially all, of the rhodium-containing catalyst composition is epoxide-free.

At least a portion of the rhodium-containing catalyst composition may include an organo-containing cation and be formed substantially without the incorporation of an epoxide. Preferably, the catalyst composition is formed separate and apart from many of the components. e.g., one or more of carbon monoxide, hydrogen and the epoxide to be hydroformylated, present during the hydroformylation. More preferably, the rhodium-containing catalyst composition is formed separate and apart from the hydroformylation contacting, e.g., in equipment other than that used for the hydroformylation. In one embodiment, the catalyst composition is formed prior to the hydroformylation.

Another broad aspect of the present invention involves a composition which comprises cations, including rhodium-containing cations, and rhodium-containing anions and has catalytic activity for promoting the hydroformylation of an epoxide. The cations are preferably rhodium-free This composition is preferably substantially epoxide-free. The composition may include an acid, preferably present in an amount so that the molar ratio of acid to rhodium is less than about 1, more preferably less than about 0.6. In one embodiment, at least a portion of the composition is derived substantially without the incorporation of an epoxide, and/or is substantially alkali metal cation free. The composition may be used in the present 1,3-diol/3-hydroxyaldehyde production process, and may be formed prior to the hydroformylation.

In a further broad aspect, the present invention is directed to a process for producing rhodium-containing compositions, e.g., epoxide hydroformylation catalysts. This process comprises contacting, e.g., in a liquid medium substantially free of epoxide, a rhodium source, and one or more components capable of forming cations at the contacting conditions, preferably an ionic component including an organo-containing cation, and preferably an acid at conditions effective to produce a rhodium-containing composition in which rhodium is present in an anion and which has catalytic activity for promoting the hydroformylation of an epoxide. When an acid is used, the molar ratio of acid to rhodium is preferably less than about 1, more preferably less than about 0.6. In one embodiment, the organo-containing cation is derived substantially without incorporation of any epoxide. When viewed as part of the 1,3-diol/3-hydroxyaldehyde production process, the present rhodium-containing catalyst composition production process is preferably performed separate and apart from the hydroformylation. Thus, the catalyst composition can be produced at conditions best suited for catalyst production using raw or feed materials which are economically attractive for such catalyst production, while the hydroformylation can occur without an induction period and without using any of the relatively valuable epoxide for catalyst production.

These and other aspects and advantages of the present invention are set forth in the following detailed description, examples and claims.

DETAILED DESCRIPTION OF THE INVENTION

The process of the present invention provides a process for the manufacture of 1,3-diols and/or 3-hydroxyaldehydes, which can be used as precursors for 1,3-diols, through the hydroformylation of epoxides. The desired 1,3-diols and 3-hydroxyaldehydes therefore contain one more carbon atom and one or more oxygen atom than the epoxide. Thus, for example, when the epoxide reactant is ethylene oxide, containing 2 carbon atoms and one oxygen atom, the desired product 1,3-diol is 1,3-propanediol, and the desired product 3-hydroxyaldehyde is 3-hydroxypropionaldehyde, each of which contain 3 carbon atoms and two oxygen atoms. As used herein, the terms "1,3-diol" and "3-hydroxyaldehyde" refer not only to the monomeric forms of these compounds, but also to oligomeric forms, e.g., in which the degree of polymerization is up to about 10, in particular dimers, trimers and tetramers. Mixed aligomers of 1,3-diols and 3-hydroxyaldehydes are also possible and are included within the scope of such terms.

The suitable epoxides have the general formula

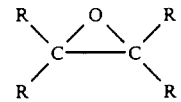

wherein each R is selected from hydrogen, monovalent aliphatic or aromatic groups containing 1 to about 12 carbon atoms, and divalent aliphatic groups containing 4 to about 6 carbon atoms and a bond with another R which is divalent. For example, when one R is a divalent saturated aliphatic group having 4 carbon atoms and one R bonded to each of the carbon atoms in the above formula is hydrogen, then the epoxide is cyclohexene oxide. Examples of specific epoxides which are useful in the present invention include ethylene oxide, propylene oxide, 1,2-epoxyoctane, cyclohexene oxide, and styrene oxide. The epoxide may be present during, particularly at the start of, the hydroformylation step of the present invention in widely varying amounts, for example, at a concentration in the range of about 0.01% to about 95%, preferably about 0.5% to about 75%, by weight based on the total weight of reactants, catalyst and liquid medium present during this step.

The hydroformylation reaction preferably takes place in the presence of, e.g., in, a suitable liquid medium, which is preferably a solvent for the epoxide and rhodium-containing catalyst. Among the suitable liquid media are aliphatic hydrocarbon components, aromatic hydrocarbon components, including benzene, toluene, xylenes and the like, ethers, including high molecular weight ethers, polyethers, especially glycol polyethers, and cyclic ethers, amides, sulfones, alcohols, ketones, esters and mixtures thereof. Specific examples of suitable liquid media include glyme (dimethoxyethane), diglyme, tetraglyme (the dimethyl ether of tetraethylene glycol), tetrahydrofuran, and oils, e.g., such as those sold under the trademark UCON by Union Carbide Corporation, which comprise mixed glycol polyethers of ethylene and propylene glycol subunits.

The liquid medium preferably solubilizes the catalyst and the epoxide reactant. Preferred liquid media do not substantially react with any of the other components present during the hydroformylation. In polar liquid media many of the components of the present catalyst compositions are often present as individual charged species, e.g., ions and the like. In non-polar liquid media these components are often present as ion pairs. Such components are referred to herein, regardless of the type of liquid medium being employed, as individual charged species, it being understood that such components may not be present as such, e.g., may be present in an ion pair. For lower molecular weight epoxides, e.g., ethylene oxide, liquid media such as glyme, tetraglyme, tetrahydrofuran, and the like and mixtures thereof are useful. For higher molecular weight epoxides, petroleum ethers and hydrocarbon materials such as benzene, toluene and xylenes, may be appropriate.

The rhodium source which is employed to make the present catalyst composition may be in the form of rhodium metal, rhodium salts, and/or rhodium complexes. Among the rhodium sources useful in the practice of the present invention are those selected from one or more of rhodium metal, rhodium oxides, $RhI_3$, $RhBr_3$, $RhCl_3$, $Rh(acac)_3$, $Rh(CO)_2acac$, $Rh_6(CO)_{16}$, $[RhCl(CO)_2]_2$ and $Rh(NO_3)_3$, wherein acac represents acetylacetonate. Rhodium may be used as a pre-formed anion, as for example $Rh_6(CO)15^{2-}$ and other similar anionic rhodium cluster salts. If the rhodium source includes rhodium in an anionic species, an acid, as described herein, should be included in making the present rhodium-containing catalyst composition.

The concentration of rhodium in the hydroformylation step may vary depending, for example, on the specific epoxide and liquid medium being employed and/or the contacting conditions. Such concentration is preferably in the range of about 100 ppm to about 10,000 ppm by weight, calculated as elemental rhodium, based on the total weight of liquid medium and epoxide present during the hydroformylation reaction.

Acids can be important in the production of the present rhodium-containing catalysts. Protonic acids are particularly useful. Medium or strong acids are preferably for use in the present invention. The acid preferably acts to promote or facilitate the formation of the rhodium-containing catalyst composition, e.g., the rhodium-containing anion associated with one or more organo-containing cations.

Suitable acids for use in this invention include such strong acids as sulfuric acid, phosphoric acid, hydroiodic acid, hydrochloric acid, hydrobromic acid, p-toluene sulfonic acid, trifluoroacetic acid and the like and mixtures thereof. Medium acids suitable for use include carboxylic acids such as benzoic acid, acetic acid, propionic acid, acidic salts, such as sodium dihydrogen phosphate, and the like and mixtures thereof. Phosphoric acid is a specific example of a useful acid. The amount of acid employed is sufficient to promote or facilitate the formation of the rhodium-containing catalyst composition. Such amount may vary depending, for example, on the specific acid and rhodium source being employed. The molar ratio of acid to rhodium may be in the range of about 0.1 to about 10. However, very advantageous results, e.g., in terms of reaction rates and product selectivities, are achieved using sufficient acid so that the molar ratio of acid to rhodium is preferably less than about 1, more preferably less than about 0.6 and still more preferably in the range of about 0.2 to about 0.6.

At least a portion of the present rhodium-containing catalyst compositions are preferably substantially alkali metal ion free. In fact, the present 1,3-diol/3-hydroxyaldehyde production process, in particular, the hydroformylation step itself, is preferably conducted in the substantial absence of alkali metal ion. The rhodium-containing catalyst composition is preferably such that the rhodium is present in an anionic species or in an anion.

In one important embodiment of the present invention, at least a portion, e.g., at least about 10%, of the presently useful rhodium-containing catalyst composition is formed separate and apart from the hydroformylation step, e.g., prior to the hydroformylation step, and/or in the substantial absence of the combination of epoxide, carbon monoxide and hydrogen used in the hydroformylation step, and/or substantially without the incorporation of an epoxide, in particular the epoxide which is to be hydroformylated. As used herein, a composition made or prepared without the incorporation of an epoxide refers to a composition which is derived from materials other than an epoxide. That is, the composition includes no epoxide and no components derived from an epoxide. Preferably, at least a major portion, i.e., at least about 50%, and more preferably substantially all, of the catalyst composition is formed separate and apart from the hydroformylation step, and/or in the substantial absence of the combination of epoxide, carbon monoxide and hydrogen used in the hydroformylation step, and/or is substantially alkali metal cation free and/or is formed substantially without the incorporation of an epoxide. A composition formed substantially without the incorporation of an epoxide and including substantially no epoxide, per se, is substantially epoxide free.

In one embodiment, the rhodium-containing catalyst composition is produced by a process comprising contacting a rhodium source and one or more components capable of forming cations at the contacting conditions, preferably an ionic component including an organo-containing cation, e.g.. as described herein, and preferably an acid, preferably in a liquid medium, e.g., such as described herein, at conditions to form a rhodium-containing composition in which rhodium is present in an anion and which has catalytic activity for promoting the hydroformylation of an epoxide.

In one embodiment, as noted above, the rhodium-containing catalyst composition is derived from an ionic component which includes one or more organo-containing cations. The ionic component is preferably such that its organo-containing cation can be associated, e.g., other than by covalent bonding, with the rhodium-containing anionic species in the rhodium-containing composition. For example, such ionic components preferably include an anion having sufficient basicity to facilitate formation of an anionic species containing rhodium. The specific anion selected depends, for example, on the specific rhodium source, acid, if any, and liquid medium being employed. Preferably, the ionic component is soluble in the liquid medium. Anions associated with medium and strong acids are one class of anions useful in the present ionic components. Specific examples include halides, sulfates. phosphates, and carboxylates, in particular low molecular weight carboxylates such as formates, acetates, and the like. The organo containing cation can include an element from group Va or group VIa of the periodic chart. One particularly useful group of organo-containing cations are those which have a formula selected from

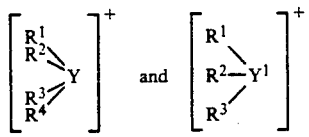

wherein Y is a polyvalent element of group Va of the periodic chart, in particular selected from nitrogen, phosphorus and arsenic, $Y^1$ is an element of group VIa of the periodic chart, each of $R^1$, $R^2$, $R^3$ and $R^4$ may be the same or different and may combine to form cyclic structures. For example, each of $R^1$, $R^2$, $R^3$ and $R^4$ may be selected from hydrogen and hydrocarbyls which may be substituted or unsubstituted and contain at least 1 carbon atom and, preferably, at least one, and most preferably all, of the hydrocarbyl $R^1$, $R^2$, $R^3$ and $R^4$ contains at least about 4 carbon atoms, e.g., about 4 to 70 carbon atoms, and sometimes about 4 to 20 carbon atoms. However, at least one of the $R^1$, $R^2$, $R^3$ and $R^4$ substituents must be hydrocarbyl-containing.

The hydrocarbyl substituents may be aliphatic, substituted aliphatic, aromatic or substituted aromatic and include, for example, n-hexyl, cyclohexyl, phenyl, benzyl, naphthyl, and the like. Illustrative of the quaternary ammonium and quaternary phosphonium moieties are tetrahydrocarbyl ammoniums, e.g., tetramethyl ammonium, tetraethyl ammonium, tetra-n-propyl ammonium, tetra-n-butyl ammonium, tetra-isobutyl ammonium, trimethyl butyl ammonium, tetraheptyl ammonium, cetyltrimethyl ammonium, tetraphenyl ammonium, trimethybenzl ammonium, tetrabenzyl ammonium, tetradodecyl ammonium, tetraoctadecyl ammonium, and the like; trihydrocarbyl ammoniums, e.g , trimethyl ammonium, triethyl ammonium, triphenyl ammonium, tridodecyl ammonium, trioctadecyl ammonium, and the like; dihydrocarbyl ammoniums, e.g., dimethyl ammonium, diethyl ammonium, di-n-butyl ammonium, di-n-heptyl ammonium, diphenyl ammonium, dibenzyl ammonium, didodecyl ammonium, dioctadecyl ammonium, and the like; hydrocarbyl ammoniums, e.g., methyl ammonium, n-butyl ammonium, dodecyl ammonium, octadecyl ammonium, phenyl ammonium, benzyl ammonium, and the like; tetrahydrocarbyl phosphoniums, e.g., tetramethyl phosphonium, tetraethyl phosphonium, tetra-n-propyl phosphonium, tetra-n-butyl phosphonium, tetra-isobutyl phosphonium, trimethyl butyl phosphonium, tetraheptyl phosphonium, tetraphenyl phosphonium, tetrabenzyl phosphonium, tetradodecyl phosphonium, tetraoctadecyl phosphonium, and the like; trihydrocarbyl phosphoniums, e.g., trimethyl phosphonium, triethyl phosphonium, triphenyl phosphonium, tridodecyl phosphonium, trioctadecyl phosphonium, and the like; dihydrocarbyl phosphoniums, e.g., dimethyl phosphonium, diethyl phosphonium, di-n-butyl phosphonium, di-n-heptyl phosphonium, diphenyl phosphonium, dibenzyl phosphonium, didodecyl phosphonium, dioctadecyl phosphonium, and the like; hydrocarbyl phosphoniums, e.g., methyl phosphonium, n-butyl phosphonium, dodecyl phosphonium, octadecyl phosphonium, phenyl phosphonium, benzyl phosphonium, and the like.

Another group of organo-containing cations includes the bis(hydrocarbyl-phosphine)iminiums represented by the formula:

$$[(R_3^5P)_2N]^+$$

wherein each $R^5$ may be the same or different and may be the same as set for $R^1$ to $R^4$. Illustrative of bis(hydrocarbylphosphine)iminiums are bis(triphenylphosphine)iminium, bis(tribenzylphosphine)iminium, bis(trimethylphosphine)iminium, bis(tridodecylphosphine)iminium, and the like and mixtures thereof.

A further group of organo-containing cations have the formula $$[(R^7)_r-Y-R^6-Y(R^7)_r]^{2+}$$

wherein $R^6$ is alkylene of 1 to about 6 carbon atoms, each $R^7$ is independently selected from hydrogen and hydrocarbyl which may be substituted or unsubstituted, and r is 3. Illustrative examples of this group include the quaternized diamines, the quaternized diphosphines, etc. Specific members of this group include N,N'-bis(trimethyl)propylene diammonium, N,N'-bis(triphenyl)propylene diammonium, N,N'-bis (trioctadecyl)propylene diammonium, P,P'-bis(trimethyl)propylene diphosphonium, and the like and mixtures thereof.

The amount of organo-containing cations used in the catalyst producing step may vary depending, for example, on the specific organo-containing cations and contacting conditions being employed and on the rhodium-containing catalyst desired. The molar ratio of ionic component (which includes the organo-containing cation) to rhodium used in the catalyst producing step may vary widely, e.g., in the range of about 0.1 to about 100. The amount of organo-containing cations present is preferably at least sufficient to become associated with the rhodium-containing entity, e.g., the rhodium-containing anion, present to provide the desired catalyst composition. Excesses of organo-containing cations, e.g., on the order of at least about 50% or at least about 100% or more, may be utilized, for example, to provide an increased rate of rhodium-containing catalyst production.

In another useful embodiment, the component capable of forming cations at the catalyst producing conditions is selected from phosphines, epoxides and mixtures thereof. In this embodiment, an acid is used such that the molar ratio of acid to rhodium less than about 0.6, preferably in the range of about 0.2 to about 0.6. A two stage catalyst producing contacting can be used. Thus, the rhodium source, acid and a phosphine can be contacted prior to being contacted with an epoxide at epoxide hydroformylation conditions. This process approach is similar to that in Murphy et al U.S. Pat. No. 4,873,378 except that the molar ratio of acid to rhodium used in the present invention is much more narrowly defined. Molar ratios of acid to rhodium as set forth above have surprisingly been found to provide advantageously increased product, 1,3-diol and/or 3-hydroxyaldehyde, formation rates and selectivities from the epoxide hydroformylation reaction.

The phosphines which may be employed in the present invention have the formula $$PR^8R^9R^{10}$$

wherein $R^8$, $R^9$, and $R^{10}$ are all independently selected from the group consisting of aliphatic, substituted aliphatic, aromatic, and substituted aromatic radicals. Preferably $R^8$, $R^9$, and $R^{10}$ are all alkyl groups containing about 1 to about 12 carbon atoms. Particularly preferred alkyl groups include methyl, ethyl, n-propyl, iso-propyl, n-butyl, iso-butyl, secbutyl, and cyclohexyl. Aryl and mixed aryl/alkyl phosphines may be used in the present invention, but their efficacy is dependent upon the particular reaction conditions employed. The trialkylphosphines are preferred. One specific phosphine is tricyclohexylphosphine.

The amount of phosphine, if any, employed in the present invention is not narrowly critical. For example, a molar ratio of rhodium to phosphine in the range of about 0.1 to about 10, preferably about 0.25 to 4, may be employed. A molar ratio of rhodium to phosphine of about 1 is useful.

The conditions at which the catalyst producing step takes place are such that the desired rhodium-containing catalyst composition is formed. This contacting preferably takes place in a liquid medium, which preferably acts as a solvent for the rhodium-containing catalyst composition and which more preferably acts as a solvent for the rhodium source and other components, e.g., the ionic component including the organo-containing cation, used to produce the rhodium-containing composition. In one particularly useful embodiment, the liquid medium used in the catalysts producing contacting has substantially the same chemical composition as the liquid medium used in the epoxide hydroformylation step.

The conditions at which the catalyst producing contacting step takes place may be similar to those used in the hydroformylation step. In one embodiment, the relatively high pressures often utilized in the hydroformylation step are not required to produce an effective rhodium-containing catalyst composition. Sufficient pressure is preferably provided to maintain the liquid medium substantially in the liquid state. For example, a pressure of about atmospheric to about 50 psig may be employed.

The molar ratio of carbon monoxide to hydrogen employed in the epoxide hydroformylation step may vary widely and may be in the range of about 0.1 to about 10.

The pressure employed during the epoxide hydroformylation is not critical and may vary provided that 1,3-diol is formed. This pressure may be in the range of about atmospheric or less, preferably at least about 200 psig, to about 10,000 psig, more preferably about 500 to about 3,000 or about 4,000 psig.

The temperature at which the epoxide hydroformylation occurs is not critical and may vary provided that at least one of a 1,3-diol and a 3-hydroxyaldehyde, preferably a 1,3-diol is formed. Increasing temperature provides increased reaction rates. However, increasing temperatures may have an adverse effect on selectivity. Thus, the temperature is preferably chosen to achieve both acceptable reaction rates and acceptable selectivities. Preferred temperatures are in the range of about 50° C. to about 200° C., more preferably about 80° C. to about 150° C.

Water may be advantageously included during the epoxide hydroformylation step. However, if the amount of water is increased beyond a given level, poorer yields of desired products may result. The amount of water employed, if any, may vary depending, for example, on the epoxide being contacted, the rhodium-containing catalyst employed, and the reaction system and hydroformylation conditions employed. Water concentrations may be, for example, in the range of 0% to about 25% by weight, based on the total of the liquid medium and water present.

The 1,3-diol and 3-hydroxyaldehyde, if any, produced in the hydroformylation are recovered, e.g., using one or more conventional recovery techniques, from the liquid medium and other components which are present during or after the contacting. Further, the 3-hydroxyaldehyde can be hydrogenated, e.g., using conventional hydrogenation processing, to yield additional amounts of 1,3-diol.

The hydrogenation step is usually conducted under specified conditions of time and temperature. Preferably, hydrogenation temperature is in the range of about 90° to about 170° C., preferably for a period of time in the range of about 0.5 to about 4 hours. The hydrogenation reaction can be carried out with or without a hydrogenation liquid medium. The hydrogenation liquid medium preferably is water, although nonreactive polar organic solvents, such as dimethoxyethane and the like, can be used. The pressure employed during hydrogenation is preferably in the range of about 500 to about 2,000 psig. The catalyst used in the hydrogenation step can be any of the well known hydrogenation catalysts used in the art, such as Raney nickel, palladium, platinum, ruthenium, rhodium, cobalt and the like. It is desirable to employ as the hydrogenation catalyst a metal or a compound of a metal which may be easily and economically prepared, which has a high degree of activity, and which retains this activity for extended periods of time. The hydrogenation catalyst may be employed in a finely divided form and dispersed throughout the reaction mixture, or it may be employed on a support or carrier material such as diatomaceous earth, clay, alumina, and the like. The amount of hydrogenation catalyst used is preferably in the range of about 1% to about 10% by weight of the 3-hydroxyaldehyde to be hydrogenated.

The present invention is further illustrated by the following non-limiting examples

EXAMPLE 1

A hydroformylation catalyst was synthesized by combining 0.52 g of rhodium dicarbonyl acetylacetonate [Rh(CO)$_2$(acac)], 0.643 g of tetrabutylphosphonium acetate [Bu$_4$P][OAc], 0.13 g of phosphoric acid H$_3$PO$_4$, and 5 cc of water in 80 cc of dimethyoxyethane. This catalyst was tested as follows.

A stirred 300 cc autoclave, made of a suitably resistant metallic alloy such as stainless steel or Hastelloy—C$^R$, and equipped with internal cooling coils, a thermocouple and a pressure measuring device was used for the treating. The catalyst, solvent and ethylene oxide were mixed in a Schlenk flask, and then pressurized into the autoclave through a valve in the head of the autoclave. The autoclave was then mounted in position and the appropriate amount of a mixture of carbon monoxide and hydrogen was introduced. The autoclave was heated to the desired temperature, and the pressure was adjusted, as necessary to maintain the desired pressure, by further additions of the CO/H$_2$ mixture or by venting. As the hydroformylation reaction progressed, additional amounts of the CO/H$_2$ mixture were added until the desired gas consumption or reaction time was achieved. After the reaction, the autoclave was cooled, e.g., to about −40° C., and excess gas pressure was vented. After warming to about 0° C., the autoclave was opened and the contents analyzed, as appropriate.

Using the catalyst described above, 10 g of ethylene oxide was contacted in the autoclave with the catalyst and solvent at 110° C. and 1000 psi pressure of a $CO/H_2$ mixture having a mole ratio of 1 CO to 2 $H_2$. Gas uptake began substantially immediately and no induction period was apparent.

This reaction resulted in a selectivity of ethylene oxide to 1,3-propanediol (and 3-hydroxypropionaldehyde) of 36 mole %. 1,3-Propanediol (and 3-hydroxypropionaldehyde) was formed at a rate equal to 0.05 moles/liter/hour.

EXAMPLE 2

A hydroformylation catalyst was synthesized by combining 0.50 g of $[Rh(CO_2)(Acac)]$, 0.88 g of 2-hydroxyethyltricyclohexylphosphonium dihydrogenphosphate $[Cy_3PCH_2CH_2OH][H_2PO_4]$, 0.13 g of $H_3PO_4$ and 5 cc of water in 80 cc of dimethoxyethane.

Using this catalyst, Example 1 was repeated. An induction period of about 50 minutes was apparent before gas uptake began. The rate of formation of 1,3-propanediol (and 3-hydroxypropionaldehyde) (not including the time of the induction period) was 0.02 moles/liter/hour, and the selectivity to 1,3 propanediol (and 3-hydroxypropionaldehyde) was 57 mole %.

EXAMPLES 3 TO 8

Example 2 was repeated a series of times, each time using an equimolar amount of one of the listed materials in place of $[Cy_3PCH_2CH_2OH][H_2PO_4]$ in the synthesis of the catalyst. Except as indicated, gas uptake began substantially immediately and no induction period was apparent.

Results of these tests were as follows:

EXAMPLE 9 (COMPARATIVE)

A hydroformylation catalyst precursor was synthesized by combining 0.51 g of $[Rh(CO)_2(acac)]$, 0.53 g of tricyclohexylphosphine $[(Cy)_3P]$, 0.13 g of $H_3PO_4$, 5 cc of water, and 0.1 g of hydroquinone in 80 g of tetraglyme solvent. This formulation was substantially the same as that reported in Example 6 of Murphy et al U.S. Pat. No. 4,873,378.

Example 1 was repeated using the catalyst precursor prepared above instead of the catalyst prepared in Example 1. An induction period of about 30 minutes occurred before gas uptake began. During this induction period, it is believed that the catalyst precursor reacted with ethylene oxide to form an active ethylene oxide hydroformylation catalyst which itself includes ethylene oxide molecules and/or one or more parts thereof. Results of this test were a selectivity to 1,3-propanediol of 59% and a rate (not including the induction period) of 1,3-propanediol formation of 0.08 moles/liter/hour.

These selectivity and rate results are quite comparable to the results achieved using catalysts of the present invention, e.g., Examples 1 to 7. However, the present system advantageously does not require an induction period and/or does not require ethylene oxide consumption to produce the catalyst, as does the catalyst precursor used in this Example 9.

EXAMPLE 10 (COMPARATIVE)

A composition was synthesized by combining 2 mmol of $[Rh(CO)_2(acac)]$ and 2 mmol of tetrabutylammonium tetraphenylborate $[Bu_4N][BPh_4]$ in 80 cc of dimethoxyethane. Example 1 was repeated except that this composition was used instead of the hydroformylation catalyst synthesized in Example 1. Substantially no ethylene oxide hydroformylation occurred. It is believed that the ionic component $[Bu_4N][BPh_4]$, and in particular the anion $[BPh_4]^-$, has insufficient basicity to facilitate the

| Example | Material | Selectivity to 1,3-Propanediol (and 3-Hydroxypropionaldehyde), mole % | Rate Of Formation 1,3-Propanediol (and 3-Hydroxypropionaldehyde), moles/liter/hour |
|---|---|---|---|
| 3 | $[(Ph_3P)_2N]Cl^{(1)}$ | 36 | 0.07 |
| 4 | $[Bu_4P]Br^{(2)}$ | 47 | 0.05 |
| 5 | $[Bu_4P]OAc^{(3)}$ | 36 | 0.05 |
| 6 | $[Bu_4N]I^{(4)}$ | 32 | 0.06 |
| 7 | $[Bu_3PCH_2CH_2OH][H_2PO_4]^{(5)}$ | 33 | 0.02 |
| 8 (Comparative) | $CsOAc^{(6)}$ | 14 | 0.03 |

$^{(1)}$Bis(triphenylphosphine)iminium chloride
$^{(2)}$Tetrabutylphosphonium bromide
$^{(3)}$Tetrabutylphosphonium acetate
$^{(4)}$Tetrabutylammonium iodide
$^{(5)}$2-Hydroxyethyltributylphosphonium dihydrogenphosphate
$^{(6)}$Cesium acetate In Example 7, an induction period of about 40 minutes occurred before gas uptake began. The rate indicated does not include this induction period.

The results indicate that the inclusion of relatively large organo-containing cations provide ethylene oxide hydroformylation catalysts which are active and selective for 1,3-propanediol (and 3-hydroxypropionaldehyde) formation. Comparing Examples 1 to 7 with Example 8, catalysts containing such organo-containing cations have increased selectivities relative to alkali metal cations, e.g., as disclosed in Murphy et al U.S. Pat. No. 4,873,379.

formation of an anionic species including rhodium. As a result, the rhodium-containing species is substantially ineffective as an ethylene oxide hydroformylation catalyst.

EXAMPLE 11 (COMPARATIVE)

The material benzyltriphenylammonium tetracarbonylrhodate $[PhCH_2NPh_3][Rh(CO_4)]$, without any acid in dimethoxyethane was evaluated as an ethylene oxide hydroformylation catalyst, using the test procedure outlined in Example 1.

This material was found to be substantially inactive, having a rate of formation of 1,3-propanediol (and 3- hydroxypropionaldehyde) of only 0.003 moles/liter/hour

EXAMPLES 12 TO 14

Example 11 was repeated three (3) times except that an acid, identified below, was included during catalyst synthesis. In each instance, gas uptake substantially began immediately and no induction period is apparent.

Results of these tests were as follows:

| Example | Acid | Selectivity to 1,3-Propanediol (and 3-Hydroxypropionaldehyde), moles % | Rate of Formation 1,3-Propanediol (and 3-Hydroxypropionaldehyde), moles/liters/hour |
|---|---|---|---|
| 12 | Acetic acid | 32 | 0.006 |
| 13 | Trifluoroacetic acid | 23 | 0.006 |
| 14 | Imidazolium acetate | 38 | 0.027 |

These results indicate that an acidic component is useful in preparing the present catalysts. Also, the effectiveness of the catalyst produced may depend, to some extent, on the specific acid or acids used.

EXAMPLES 15 TO 21

A series of tests were run to demonstrate the effect of the acid to rhodium ratio on epoxide hydroformylation.

Seven (7) catalysts were synthesized by combining 2 mmol of [Rh (CO)$_2$(Acac)], 2 mmols of PCy$_3$, a variable amount of phosphoric acid, and 5 cc of water in 80 cc of tetraglyme. Each of these catalysts was tested as set forth in Example 1.

Results of these tests were as follows:

| Example | H$_3$PO$_4$/Rh, molar | Selectivity to 1,3-Propanediol (and 3-Hydroxypropionaldehyde), mole % | Rate of Formation 1,3-Propanediol (and 3-Hydroxypropionaldehyde), moles/liter/hour[1] | Estimated Induction Period, |
|---|---|---|---|---|
| 15 | 0 (No H$_3$PO$_4$) | 53 | 0.10 | 70 |
| 16 | 0.125 | 64 | 0.13 | 50 |
| 17 | 0.25 | 74 | 0.16 | 80 |
| 18 | 0.50 | 72 | 0.16 | 75 |
| 19 | 0.75 | 69 | 0.15 | 80 |
| 20 | 1.00 | 67 | 0.13 | 75 |
| 21 | 1.25 | 56 | 0.10 | 75 |

[1]Includes time in induction period.

These results indicate that substantial improvements in both selectivity and rate are obtained by maintaining the molar ratio of acid to rhodium less than about 0.6. In particular, compare Examples 19 and 20 with Examples 17 and 18. This is especially surprising in view of Murphy et al U.S. Pat. No. 4,873,378 which teaches that the preferred molar ratio of acid to rhodium is approximately 1 to 1, and that variations of the molar ratio by factors of 2–5 only result in mildly deleterious effects. The lowest acid to rhodium molar ratio (where acid was present) disclosed in any of the Examples of Murphy et al U.S. Pat. No. 4,873,378 was 0.65 (Example 7). To the contrary, the above data demonstrate that substantial beneficial effects are achieved at acid to rhodium molar ratios less than about 0.6.

While this invention has been described with respect to various specific examples and embodiments, it is to be understood that the invention is not limited thereto and that it can be variously practiced within the scope of the following claims.

What is claimed is:

1. A process for producing a 1,3-diol or a 3-hydroxyaldehyde comprising:

contacting a combination of (a) an epoxide having the formula

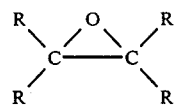

wherein each R is selected from hydrogen, monovalent aliphatic or aromatic groups containing 1 to about 12 carbon atoms, and divalent aliphatic groups containing 4 to about 6 carbon atoms and a bond with another R which is divalent, (b) carbon monoxide and (c) hydrogen in the presence of (d) a rhodium-containing catalyst composition effective to promote the hydroformylation of said epoxide at conditions effective to form at least one of a 1,3-diol and a 3-hydroxyaldehyde, said contacting occurring in the substantial absence of a promoting amount of alkali metal cations, and at least a portion of said rhodium-containing catalyst composition being formed substantially without incorporation of said epoxide.

2. The process of claim 1 wherein at least a major portion of said rhodium-containing catalyst composition is formed substantially without incorporation of said epoxide.

3. The process of claim 1 wherein substantially all of said rhodium-containing catalyst composition is formed substantially without incorporation of said epoxide.

4. The process of claim 1 wherein said rhodium is present in an anionic species.

5. The process of claim 4 wherein said anionic species is associated with an organo-containing cation.

6. The process of claim 1 wherein said contacting takes place in the presence of an organo-containing cation which includes an element from group Va or group VIa of the periodic chart.

7. The process of claim 6 wherein said organo-containing cation is selected from the group consisting of:

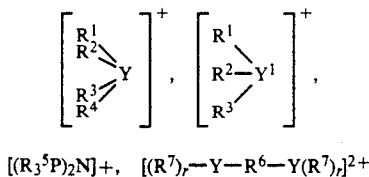

$[(R_3^5P)_2N]+$,   $[(R^7)_r-Y-R^6-Y(R^7)_r]^{2+}$ and mixtures thereof, wherein Y is an element of group Va of the periodic chart, $Y^1$ is an element of group VIa of the periodic chart; $R^1$, $R^2$, $R^3$ and $R^4$ are independently selected from the group consisting of H and hydrocarbyl groups having from 1 to about 70 carbon atoms, provided that at least one of said substituents of any of said organo-containing cation is a hydrocarbyl group having from 1 to about 70 carbon atoms; each $R^5$ is independently selected from the group consisting of H and hydrocarbyl groups having from 1 to about 70 carbon atoms, provided that at least one of said substituents is a hydrocarbyl group having from 1 to about 70 carbon atoms; $R^6$ is an alkylene group having from 1 to about 6 carbon atoms; each $R^7$ is independently selected from the group consisting of H and hydrocarbyl groups having from 1 to about 70 carbon atoms; and r is 3.

8. The process of claim 1 wherein said epoxide is ethylene oxide and said 1,3-diol is 1,3-propanediol and said 3-hydroxyaldehyde is 3-hydroxypropionaldehyde.

9. A process for producing a 1,3-diol or a 3-hydroxyaldehyde comprising:

contacting a combination of (a) an epoxide having the formula

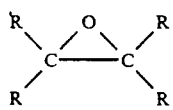

wherein each R is selected from hydrogen, monovalent aliphatic or aromatic groups containing 1 to about 12 carbon atoms, and divalent aliphatic groups containing 4 to about 6 carbon atoms and a bond with another R which is divalent, (b) carbon monoxide and (c) hydrogen in the presence of (d) a rhodium-containing catalyst at least a portion of said rhodium-containing catalyst effective to promote the hydroformylation of said epoxide at conditions effective to form at least one of a 1,3-diol and a 3-hydroxyaldehyde, said rhodium-containing catalyst composition including an organo-containing cation, at least a portion of said rhodium-containing catalyst composition being formed substantially without incorporation of said epoxide.

10. The process of claim 9 wherein at least a major portion of said rhodium-containing catalyst composition is formed substantially without incorporation of said epoxide.

11. The process of claim 9 wherein substantially all of said rhodium-containing catalyst composition is formed substantially without incorporation of said epoxide.

12. The process of claim 9 wherein said rhodium-containing catalyst composition includes rhodium present in an anionic species.

13. The process of claim 9 wherein said organo-containing cation includes an element from group Va or group VIa of the periodic chart.

14. The process of claim 10 wherein said organo-containing cation is selected from the group consisting of:

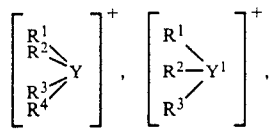

$[(R_3^5P)_2N]+$,   $[(R^7)_r-Y-R^6-Y(R^7)_r]^{2+}$ and mixtures thereof, wherein Y is an element of group Va of the periodic chart, $Y^1$ is an element of group VIa of the periodic chart; $R^1$, $R^2$, $R^3$ and $R^4$ are independently selected from the group consisting of H and hydrocarbyl groups having from 1 to about 70 carbon atoms, provided that at least one of said substituents of any of said organo-containing cation is a hydrocarbyl group having from 1 to about 70 carbon atoms; each $R^5$ is independently selected from the group consisting of H and hydrocarbyl groups having from 1 to about 70 carbon atoms, provided that at least one of said substituents is a hydrocarbyl group having from 1 to about 70 carbon atoms; $R^6$ is an alkylene group having from 1 to about 6 carbon atoms; each $R^7$ is independently selected from the group consisting of H and hydrocarbyl groups having from 1 to about 70 carbon atoms; and r is 3.

15. The process of claim 9 wherein said rhodium-containing catalyst composition is formed prior to said contacting.

16. The process of claim 9 wherein said epoxide is ethylene oxide and said 1,3-diol is 1,3-propanediol and said 3-hydroxyaldehyde is 3-hydroxypropionaldehyde.

17. A process for producing a 1,3-diol or a 3-hydroxyaldehyde comprising:

contacting a combination of (a) an epoxide having the formula

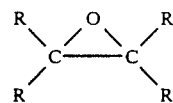

wherein each R is selected from hydrogen, monovalent aliphatic or aromatic groups containing 1 to about 12 carbon atoms, and divalent aliphatic groups containing 4 to about 6 carbon atoms and a bond with another R which is divalent, (b) carbon monoxide and (c) hydrogen in the presence of (d) a rhodium-containing catalyst composition effective to promote the hydroformylation of said epoxide at conditions effective to form at least one of a 1,3-diol and a 3-hydroxyaldehyde, at least a portion of said rhodium-containing catalyst composition being formed in the substantial absence of said combination.

18. The process of claim 17 wherein at least a major portion of said rhodium-containing catalyst composition is formed in the substantial absence of said combination.

19. The process of claim 17 wherein substantially all of said rhodium-containing catalyst composition is formed in the substantial absence of said combination.

20. The process of claim 17 wherein at least a portion of said rhodium-containing catalyst composition is formed in the substantial absence of said epoxide.

21. The process of claim 17 wherein said contacting occurs in the substantial absence of a promoting amount of alkali metal ions.

22. The process of claim 17 wherein said contacting occurs in the presence of organo-containing cations which include an element from group Va or group VIa of the periodic chart.

23. The process of claim 22 wherein said organo-containing cations are selected from the group consisting of:

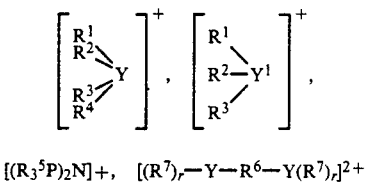

$[(R_3^5P)_2N]+$,  $[(R^7)_r-Y-R^6-Y(R^7)_r]^{2+}$ and mixtures thereof, wherein Y is an element of group Va of the periodic chart, $Y^1$ is an element of group VIa of the periodic chart; $R^1$, $R^2$, $R^3$ and $R^4$ are independently selected from the group consisting of H and hydrocarbyl groups having from 1 to about 70 carbon atoms, provided that at least one of said substituents of any of said organo-containing cation is a hydrocarbyl group having from 1 to about 70 carbon atoms; each $R^5$ is independently selected from the group consisting of H and hydrocarbyl groups having from 1 to about 70 carbon atoms, provided that at least one of said substituents is a hydrocarbyl group having from 1 to about 70 carbon atoms; $R^6$ is an alkylene group having from 1 to about 6 carbon atoms; each $R^7$ is independently selected from the group consisting of H and hydrocarbyl groups having from 1 to about 70 carbon atoms; and r is 3.

24. The process of claim 17 which further comprises forming said rhodium-containing catalyst composition in one zone and, thereafter, transferring said rhodium-containing catalyst composition to a different zone where said contacting occurs.

25. The process of claim 17 wherein said epoxide is ethylene oxide and said 1,3-diol is 1,3-propanediol and said 3-hydroxyaldehyde is 3-hydroxypropionaldehyde.

26. A process for producing a 1,3-diol or a 3-hydroxyaldehyde comprising:
contacting a combination of (a) an epoxide having the formula

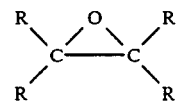

wherein each R is selected from hydrogen, monovalent aliphatic or aromatic groups containing 1 to about 12 carbon atoms, and divalent aliphatic groups containing 4 to about 6 carbon atoms and a bond with another R which is divalent, (b) carbon monoxide and (c) hydrogen in the presence of (d) a rhodium-containing catalyst composition effective to promote the hydroformylation of said epoxide at conditions effective to form at least one of a 1,3-diol and a 3-hydroxyaldehyde, said rhodium-containing catalyst being formed by a process comprising contacting a rhodium source, one or more components capable of forming cations at the conditions of said rhodium source contacting and an acid at conditions effective to form said rhodium-containing catalyst composition in which rhodium is present in an anionic species, the molar ratio of rhodium to said acid in said rhodium source contacting being less than about 0.6.

27. The process of claim 26 wherein said molar ratio is in the range of about 0.2 to about 0.6.

28. The process of claim 26 wherein said components include one or more materials selected from the group consisting of phosphines, epoxides and mixtures thereof.

29. The process of claim 26 wherein said acid is a protonic acid.

30. The process of claim 26 wherein said acid is phosphoric acid.

31. The process of claim 26 wherein said epoxide is ethylene oxide, said 1,3-diol is 1,3-propanediol and said 3-hydroxyaldehyde is 3-hydroxypropionaldehyde.

* * * * *